United States Patent [19]

Bock et al.

[11] Patent Number: 4,628,084
[45] Date of Patent: Dec. 9, 1986

[54] PROCESS FOR 3-ACYLAMINO BENZODIAZEPINES

[75] Inventors: Mark G. Bock, Hatfield; Daniel F. Veber, Ambler; Robert M. DiPardo, Lansdale, all of Pa.

[73] Assignee: Merck & Co., Inc., Rahway, N.J.

[21] Appl. No.: 815,620

[22] Filed: Jan. 2, 1986

[51] Int. Cl.$^4$ ............................................. C07D 243/24
[52] U.S. Cl. ................................... 540/509; 548/492; 564/154
[58] Field of Search ................................. 260/239.3 D

[56] References Cited

U.S. PATENT DOCUMENTS 3,344,136  9/1967  Bell et al. ................... 260/239.3 D Primary Examiner—Robert T. Bond
Attorney, Agent, or Firm—Richard A. Elder; Hesna J. Pfeiffer

[57] ABSTRACT

The present invention provides an improved process for producing 3-acylamino benzodiazepines of the formula:

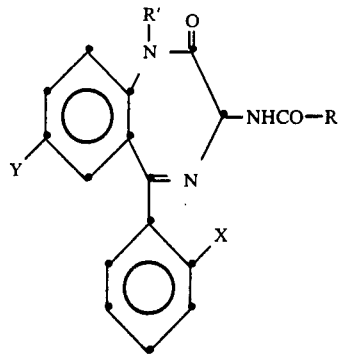

wherein:

R is loweralkyl of from 1-6 carbon atoms, aryl such as phenyl and halophenyl, aralkyl, alkyloxy, aralkyloxy, indolyl or substituted indolyl;

R' is hydrogen, loweralkyl of from 1-6 carbon atoms, carboxymethyl or carbalkoxymethyl wherein the alkoxy groups contain from 1-4 carbon atoms;

X is hydrogen or halogen;

Y is hydrogen or halogen.

These compounds are useful because of their activity as cholecystokinin (CCK) inhibitors.

5 Claims, No Drawings

PROCESS FOR 3-ACYLAMINO BENZODIAZEPINES

BACKGROUND OF THE INVENTION

Benzodiazepine analogs of the type defined in formula I hereinabove are known to be useful as CCK antagonists as disclosed in copending application Ser. No. 641,972 filed 6/10/85 were only available via multi-step and/or low yielding syntheses resulting in expensive final products. Some of these procedures are detailed in the following references. Synthesis of benzodiazepines *J. Org. Chem.* 33, 828-830 (1968), S. C. Bell et al.; *J. Org. Chem.* 33 216-220 (1968), S. C. Bell et al.; *J. Org. Chem.* 27, 3781-88 (1962), L. H. Sternbach et al.; *J. Org. Chem.* 36, 1064-68 (1971), Y. R. Ning et al.; *J. Org. Chem.* 26, 4488-97 (1961), L. H. Sternbach et al.; *Tet. Lett.* (1965) pp. 2889-91, S. C. Bell et al.; U.S. Pat. No. 3,344,136 of S. C. Bell et al.; U.S. Pat. No. 3,198,789 of S. C. Bell; U.S. Pat. No. 3,899,527 of R. J. McCaully.

DESCRIPTION OF THE INVENTION

The present invention comprises a novel, high yielding and simple procedure for preparing 3-acylamino benzodiazepine compounds and derivatives thereof starting with the well-known and readily available o-aminobenzophenone or substituted derivatives thereof.

Thus, in accordance with the following formula flow diagram:

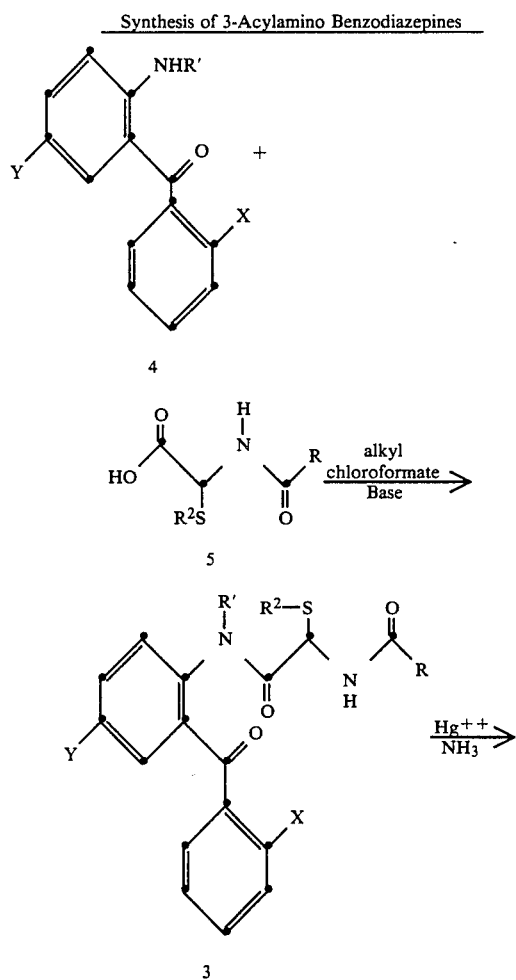

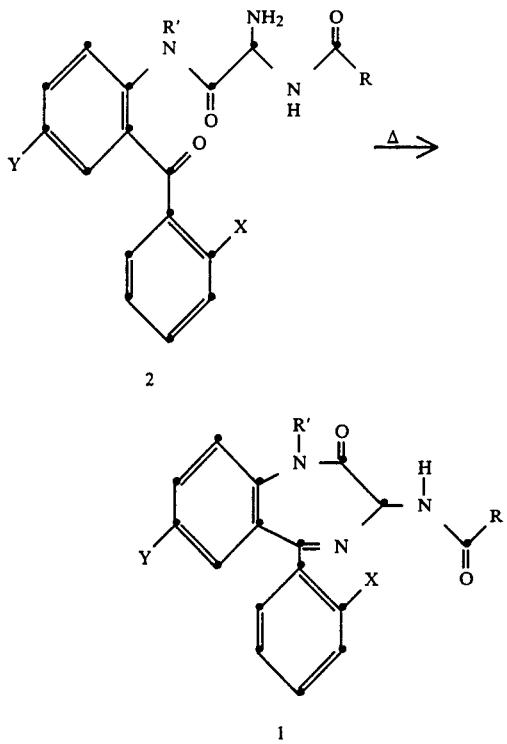

wherein:

R is loweralkyl of from 1-6 carbon atoms, aryl such as phenyl and halophenyl, aralkyl, alkyloxy, aralkyloxy, indolyl or substituted indolyl;

R' is hydrogen, lower alkyl of from 1-6 carbon atoms, or carboxymethyl or carbalkoxymethyl wherein the alkoxy groups contain from 1-4 carbon atoms;

$R^2$ is loweralkyl, aralkyl, or aryl;

X is hydrogen or halogen; and

Y is hydrogen or halogen.

In the above reaction scheme the o-amino benzophenone 4 is acylated by treatment with an amidothiol derivative of glyoxylic acid 5 to form the acyl derivative of o-amino benzophenone 3 as the first step of the synthesis. In the second step of the synthesis, the acyl derivative 3 is converted by treatment with ammonia with added mercury (II) or silver (I) salts to the amino intermediate of formula 2 which is then cyclized to form the 3-acylamino benzodiazepine 1 in the final step.

The glyoxylic acid derivatives, used as reactants in the first step of the process, are known compounds, the preparation of which are described in Tetrahedron Vol. 31, pp. 863-866, Pergamon Press 1975 in an article entitled *Amidoalkylation of Mercaptan with Glyoxylic Acid Derivatives* by U. Zoller and D. Ben-Ishai.

In accordance with the process of the present invention, o-aminobenzophenone or an o-amino-2-halobenzophenone, preferably o-amino-2-fluorobenzophenone is dissolved in an aprotic solvent such as methylene chloride and the resulting solution cooled to about 0° C. The resulting solution is then mixed with an equimolar amount of a tertiary amine such as N-methylmorpholine and a similar amount of alkyl chloroformate such as isobutylchloroformate and the reaction mixture maintained at a temperature of 0° C. for approximately 15 minutes. To the resulting reaction mixture, containing the mixed anhydride corresponding to 5, is then added dropwise an equimolar amount of the o-aminobenzophenone to produce the N-acyl derivative of o-aminobenzophenone compound 3 hereinabove. The reaction mixture is then allowed to warm to 25° C. and is stirred for about 18 hours at that temperature or heated to about 55° C. for 2.5 hours to insure completion of acylation reaction. This crude reaction mixture was then washed with aqueous citric acid, aqueous sodium bicarbonate solution and brine and after drying, the solvent removed by evaporation under reduced pressure leaving the crude product 3 in good yield as a residue.

In accordance with the second step of the synthesis of 3-acylamino benzodiazepine, the thioether substituent is first replaced with an amino group by treatment with excess ammonia in the presence of added mercury or silver salts to form intermediate 2 hereinabove. The solvent and salts are removed and the crude reaction product is cyclized in acetic acid containing ammonium acetate to produce the desired product in good yield. In a preferred instance the crude thioether 3 is dissolved in tetrahydrofuran or other solvent inert under the reaction conditions and the solution saturated with ammonia gas. A slight molar excess of mercuric chloride is added and a stream of ammonia gas passed into the reaction mixture for a period of from 1-5 hours, preferably for about 2 hours under ambient temperature condition (25° C.). The suspended solids and the solvent is then removed and the residual oily product, wherein the amino group has replaced the thiolether substituent in the N-acyl side chain of 3 is dissolved in excess acetic acid containing approximately 5 g ammonium acetate/100 ml acetic acid. The resulting solution is then protected from moisture and heated at 55° C. for 2.5 hours or stirred at 25° C. for 18 hours to produce the desired product, the 3-acylamino benzodiazepine 1, which is recovered as a solid after removal of the acetic acid by evaporation under reduced pressure and partitioning the residual material containing the desired product between ethyl acetate and 1N sodium hydroxide solution. The solid product in pure form separated from the ethyl acetate fraction in good overall yield (75% of theoretical).

The following examples are for purposes of illustration and are not in any way intended to set limits on the invention claimed. Temperatures are expressed in degrees Celsius.

EXAMPLES

Preparation of
α-Isopropylthio-N-benzyloxycarbonylglycine, 5

This material was prepared according to U. Zoller and D. Ben-Ishai, *Tetrahedron* (1975) 31, 863.

EXAMPLE 1

2-N-(α-Isopropylthio-N-benzyloxycarbonylglycinyl-)aminobenzophenone 3

α-Isopropylthio-N-benzyloxycarbonylglycine (10.54 g, 37.2 mmole) was dissolved in 400 ml of dry methylene chloride in a three-necked 500 ml flask equipped with magnetic stirrer, addition funnel, and a drying tube. The solution was cooled to 0° C. and treated with 4.1 ml (37.2 mmole) of N-methylmorpholine followed by 4.8 ml (37.2 mmole) of isobutyl chloroformate. The resulting reaction mixture was stirred at 0° C. for 15 minutes more and then treated dropwise over 20 minutes with a solution of 6.97 g (35.3 mmole) of o-aminobenzophenone in 50 ml of dry methylene chloride. The reaction mixture was slowly allowed to warm to room temperature on overnight stirring. The yellow reaction mixture was washed in succession with 10% citric acid solution (2×100 ml), saturated sodium bicarbonate solution (2×100 ml), and brine. The dried (MgSO₄) organic phase was concentrated in vacuo to afford 20 g of crude product 3. (Note: Carry out reaction in a well ventilated hood and wear protective gloves.)

EXAMPLE 2

2-N-(α-Amino-N-benzyloxycarbonylglycinyl-)aminobenzophenone, 2

The crude thioether 3 (14.0 g, 30.3 mmole) was dissolved in 200 ml of tetrahydrofuran. This solution was cooled to 0° C. and saturated with ammonia. Mercuric chloride (9.07 g, 33.4 mmole) was then added in one portion to the stirred mixture while a continuous stream of ammonia gas was bubbled into the reaction flask. After two hours the suspended solids were removed and the solvent was rotoevaporated to give crude 3 as an oil (16 g) which was used immediately without further purification. (Note: All manipulations and apparatus should be confined to a well ventilated hood.)

EXAMPLE 3

1,3-Dihydro-5-phenyl-3-benzyloxycarbonylamino-2H-1,4-benzodiazepin-2-one, 1

The crude product 2 (16 g) was dissolved in 300 ml of glacial acetic acid and treated with 14.4 g (187 mmole) of ammonium acetate. The resulting reaction mixture was then protected from moisture and stirred at room temperature overnight (or for 2.5 hours at 55° C.). The heterogeneous reaction mixture was concentrated under reduced pressure to remove most of the acetic acid and the residue was partitioned between ethyl acetate (175 ml) and 1N sodium hydroxide solution (40 ml). After stirring for 30 minutes the solids were collected and washed with ethyl acetate to afford 7.1 g of pure product. The ethyl acetate washings (containing mercury salts) were combined and concentrated to afford an additional 1.1 g of product; this represents an overall yield of 60% based on aminobenzophenone 4 and can be further raised to approximately 70-75% if the mother liquor is processed by flash chromatography on silica gel (hexane-ethyl acetate, 1:1 v/v elution.

EXAMPLE 4

1,3-Dihydro-5-(2'-fluorophenyl)-3-benzyloxycarbonylamino-2H-1,4-benzodiazepine-2-one The procedure of Examples 1-3 is repeated using o-amino-2-fluorobenzophenone as starting material and the product obtained is 1,3-dihydro-5-(2'-fluorophenyl)-3-benzyloxycarbonylamino-2H-1,4-benzodiazepine-2-one.

EXAMPLE 5

1,3-Dihydro-1-methyl-5-phenyl-3-benzyloxycarbonylamino-2H-1,4-benzodiazepine-2-one The procedure of Examples 1-3 is repeated using as starting material N-methylaminobenzophenone with production of the titled product.

EXAMPLE 6

1,3-Dihydro-1-methyl-5-(2'-fluorophenyl)-3-benzyloxycarbonylamino-2H-1,4-benzodiazepine-2-one The procedure of Examples 1-3 is repeated using as starting material N-methylamino-2'-fluorobenzophenone with resultant production of the titled product.

EXAMPLE 7

The following table lists other related 3-acylaminobenzodiazepines which may be prepared utilizing the process of the present invention and the o-aminobenzophenone or o-amino-2'-fluorobenzophenone or the 1-methyl derivatives of Examples 5, 6 or 7 as starting material followed by acylation with the appropriate acylation agent.

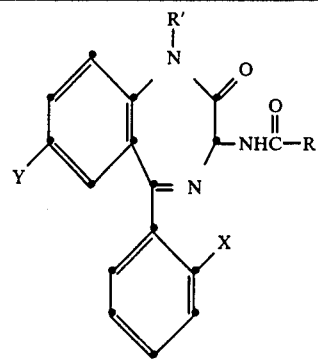

| Entry | X | Y | R' | R | m.p. |
|---|---|---|---|---|---|
| 1 | H | H | H |  | 259–260° C. |
| 2 | F | H | CH₃ | 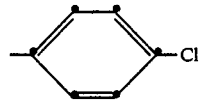 | 171.5–172° C. |
| 3 | H | H | CH₃ | 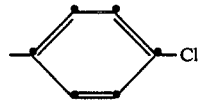 | 218–220° C. |
| 4 | F | H | H | 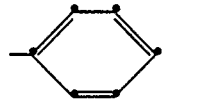 | 243–244° C. |
| 5 | F | H | H | CH₃ | 244–245° C. |
| 6 | F | H | H | 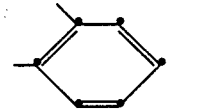 | 224–224.5° C. |
| 7 | H | H | H | 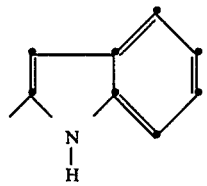 | 265–268° C. |
| 8 | F | H | CH₃ | 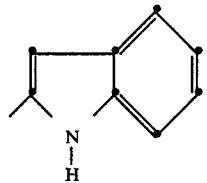 | 282–283.5° C. |
| 9 | F | H | H | 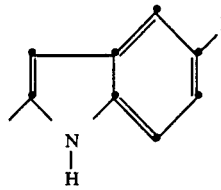 | 268–271° C. |
| 10 | F | H | H | | 290–291° C. |
| 11 | F | H | H | | 281–284° C. |
| 12 | F | H | H | | 228° C. |

-continued

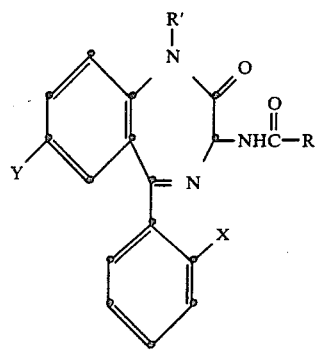

| Entry | X | Y | R' | R | m.p. |
|---|---|---|---|---|---|
| 13 | H | H | CH₃ | 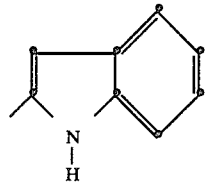 | 269–270° C. |
| 14 | H | H | CH₃ | 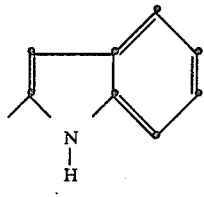 | 202.5–203° C. |
| 15 | F | H | H | 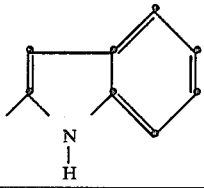 | 266–268° C. |

What is claimed is:

1. A process for the preparation of 3-acylamino benzodiazepines of the formula:

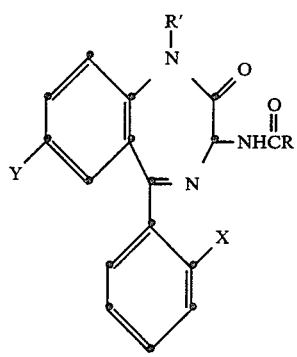

wherein X and Y are hydrogen or halogen, which comprises reacting an o-aminobenzophenone of the formula:

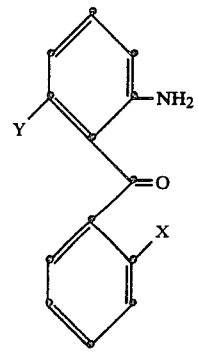

with an amidothiol derivative of glyoxylic acid of the formula:

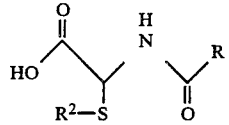

to form an N-acylbenzophenone of the formula:

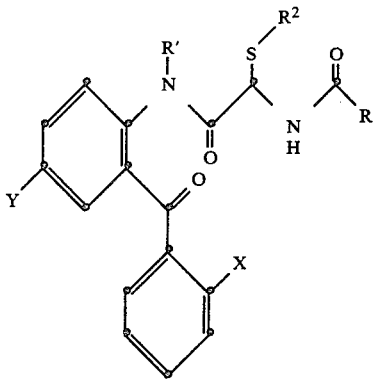

wherein:

R is loweralkyl of from 1–6 carbon atoms, aryl such as phenyl or halophenyl, aralkyl, alkyloxy or aralkyloxy, indolyl or substituted indolyl;

R' is hydrogen, loweralkyl of from 1–6 carbon atoms, carboxymethyl, or carbalkoxymethyl wherein the alkoxy groups contain from 1–4 carbon atoms;

R² is loweralkyl, aralkyl, or aryl; treating said N-acylbenzophenone with ammonia in the presence of silver or mercury salts to form a compound of the formula:

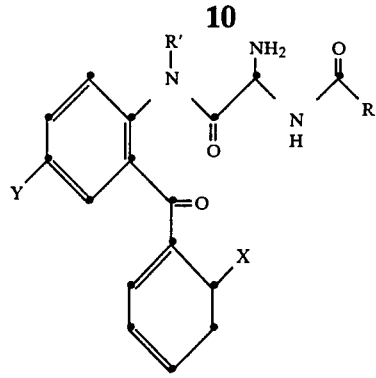
and heating said product.
2. A process according to claim 1 wherein R is benzyloxy and R' is methyl.
3. A process according to claim 2 wherein X and Y are hydrogen.
4. A process according to claim 2 wherein X and Y are halogen.
5. A process according to claim 2 wherein Y is hydrogen and X is halogen.
* * * * *